(12) United States Patent
Jablow et al.

(10) Patent No.: US 9,492,257 B2
(45) Date of Patent: Nov. 15, 2016

(54) PHOTOCATALYTIC TEETH WHITENING

(71) Applicant: JASIBO, LLC., Las Vegas, NV (US)

(72) Inventors: Jennifer Jablow, New York, NY (US); Michael Mark Muehlemann, Liverpool, NY (US)

(73) Assignee: Jasibo, LLC, Las Vegas, NV (US)

( * ) Notice: Subject to any disclaimer, the term of this patent is extended or adjusted under 35 U.S.C. 154(b) by 232 days.

(21) Appl. No.: 14/476,295

(22) Filed: Sep. 3, 2014

(65) Prior Publication Data

US 2015/0064645 A1    Mar. 5, 2015

Related U.S. Application Data

(60) Provisional application No. 61/873,088, filed on Sep. 3, 2013.

(51) Int. Cl.
| | |
|---|---|
| *A61C 1/00* | (2006.01) |
| *A61C 19/06* | (2006.01) |
| *A61C 1/08* | (2006.01) |
| *A61K 8/27* | (2006.01) |
| *A61K 8/22* | (2006.01) |
| *A61Q 11/00* | (2006.01) |

(52) U.S. Cl.
CPC ............ *A61C 19/066* (2013.01); *A61C 1/088* (2013.01); *A61K 8/22* (2013.01); *A61K 8/27* (2013.01); *A61Q 11/00* (2013.01); *A61K 2800/81* (2013.01)

(58) Field of Classification Search
CPC ................ A61C 19/066; A61C 1/088; A61K 2800/81; A61K 8/22; A61K 8/27; A61Q 11/00
See application file for complete search history.

(56) References Cited

U.S. PATENT DOCUMENTS

| | | | |
|---|---|---|---|
| 6,896,693 B2 | 5/2005 | Sullivan | |
| 8,021,148 B2 | 9/2011 | Goodson et al. | |
| 8,029,278 B1 * | 10/2011 | Levine | A61C 19/063 433/215 |
| 8,308,479 B2 * | 11/2012 | Philp, Jr. | A61C 19/063 433/215 |
| 2008/0060148 A1 | 3/2008 | Pinyayev et al. | |
| 2008/0233541 A1 | 9/2008 | De Vreese et al. | |
| 2008/0255498 A1 * | 10/2008 | Houle | A61C 17/02 604/20 |
| 2009/0148815 A1 | 6/2009 | Philp, Jr. et al. | |
| 2011/0189626 A1 | 8/2011 | Sanzari | |
| 2012/0148976 A1 | 6/2012 | Brawn | |

OTHER PUBLICATIONS

International Search Report and Written Opinion received for International Patent Application No. PCT/US2014/53884, dated Dec. 16, 2014, 9 pages.

* cited by examiner

*Primary Examiner* — George Manuel
(74) *Attorney, Agent, or Firm* — Ziegler IP Law Group, LLC

(57) ABSTRACT

The present disclosure relates to devices, methods and kits for accelerating the rate of whitening of teeth using an oxidizing agent, a photocatalytic agent, and a portable lightsource.

11 Claims, 3 Drawing Sheets

PHOTOCATALYTIC TEETH WHITENING

FIELD

The present disclosure includes devices and methods for accelerating the rate of whitening of teeth using an oxidizing agent, a photocatalytic agent, and a portable lightsource.

BACKGROUND

Professional tooth whitening is performed in a dental office and generally includes the application of high concentration peroxides with or without light activation. Home use peroxides are regulated substances that have concentrations that are generally substantially lower than those used in professional settings. Numerous products are available in the market place including Zoom!®, BriteSmile®, LaserSmile®, Beyond®, Opalescence®, Lumibrite®, LumaCool®, NUPRO®, and Niveous®. The concentration of the oxidizing agent defines the rate of whitening, and therefore home treatments have suffered from significantly lower whitening rates than that available in professional dental treatments. The present disclosure is focused on the development of a home dental product which accelerates the whitening rate by using photocatalytic methods to increase the concentrations of oxidizing agents at the time of treatment.

There is considerable literature describing teeth brightening technology including U.S. Pat. No. 5,702,250 (December 1997) to Kipke, U.S. Pat. No. 6,155,832 (December 2000) to Wiesel; U.S. Pat. No. 6,162,055 (December 2000) to Montgomery et al., U.S. Pat. No. 6,616,451 (September 2003) to Rizolu et al., U.S. Pat. No. 6,733,290 (May 2004) to West et al., U.S. Pat. No. 6,752,627 (June 2004) to Lin, U.S. Pat. No. 6,783,363 (August 2004) to Eguchi et al., U.S. Pat. No. 6,902,397 (June 2005) to Farrell et al., U.S. Pat. No. 7,004,756 (February 2006) to Andersen, U.S. Pat. No. 7,086,862 (August 2006) to Craig, U.S. Pat. No. 7,144,249 (December 2006) to Rizoin et al., U.S. Pat. No. 7,160,111 (January 2007) to Baughman, U.S. Pat. No. 7,223,270 (May 2007) to Altshuler et al., U.S. Pat. No. 7,250,155 (July 2007) to Yamaguchi et al., and U.S. Pat. No. 8,029,278 (October 2011) to Levine. Additional literature includes United States Patent Publications 2004/0193236 (September 2004), 2005/0053898 (March 2005), 2005/0064370 (March 2005), 2005/0074717 (April 2005), 2005/0158687 (July 2005), 2005/0172429 (August 2005), 2005/0202363 (September 2005), 2005/0231983 (October 2005), 2006/0019214 (January 2006), 2006/0141422 (June 2006), 2006/0194164 (August 2006), 2006/0257822 (November 2006), 2007/0003905 (January 2007), 2007/0015112 (January 2007), and 2007/0020584 (January 2007).

International Patent Application PCT/US14/34598 filed Apr. 18, 2014 and entitled "LIGHT ACTIVATED TOOTH WHITENING SYSTEM, COMPOSITION AND DELIVERY METHOD," and commonly assigned with the present application, describes certain oxidizing formulations and is herein incorporated by reference in its entirety.

SUMMARY

The aspects of the present disclosure are directed to a portable lightsource, a dental bleaching agent, and a dental bleaching method that overcome certain shortcomings associated with existing whitening products and methods. The lightsource comprises a flashing blue light illuminator coupled to a removable mouthpiece lightguide that precisely directs the light to the teeth. The teeth are separately preconditioned with a bleaching material and a catalyst. Specifically, application of the methods, compositions and devices of the present disclosure results in an increased whitening rate and shorter home treatment times. More specifically, the aspects of the present disclosure are directed to a new and novel method for accelerating the rate of hydrogen peroxide whitening for the treatment of dental stains or discolorations.

These and other aspects and advantages of the exemplary embodiments will become apparent from the following detailed description considered in conjunction with the accompanying drawings. It is to be understood, however, that the drawings are designed solely for purposes of illustration and not as a definition of the limits of the disclosure, for which reference should be made to the appended claims. Additional aspects and advantages of the disclosure will be set forth in the description that follows, and in part will be obvious from the description, or may be learned by practice of the disclosure. Moreover, the aspects and advantages of the disclosure may be realized and obtained by means of the instrumentalities and combinations particularly pointed out in the appended claims.

BRIEF DESCRIPTION OF THE DRAWINGS

The accompanying drawings illustrate presently preferred embodiments of the present disclosure, and together with the general description given above and the detailed description given below, serve to explain the principles of the present disclosure.

DETAILED DESCRIPTION OF THE EMBODIMENTS

Figure 1:
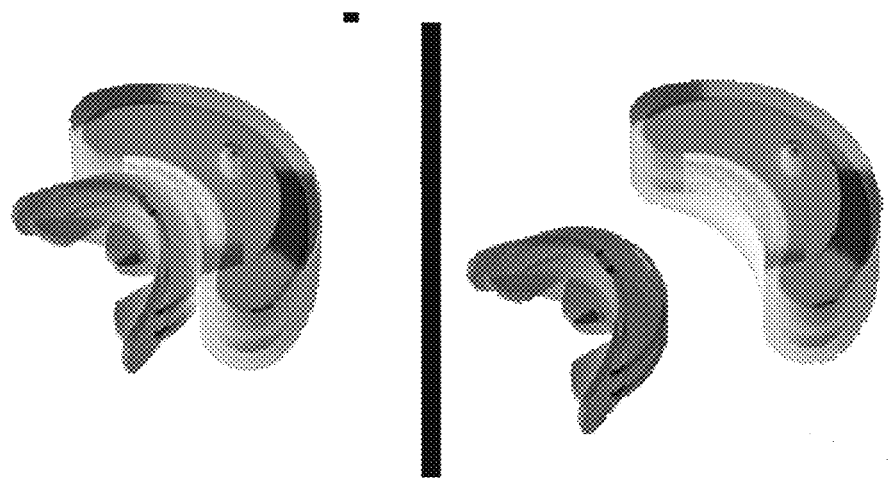
FIG. 1 illustrates an illuminating device comprised of a removable mouthpiece that acts as the lightguide for precisely directing the light to the teeth and an illuminator LED lightsource that generates the light, see FIG. 1. The optically clear mouthpiece snaps into the LED lightsource during treatment and is removed for cleaning after each treatment. This design allows for the mouthpiece to be replaced without replacing the other elements of the stem. Each mouthpiece may also be individualized to fit precisely the dental surface. It also allows for use of multiple mouthpieces so that the device may be shared among multiple family members much the same way an electric toothbrush is shared. The detachable lightsource is powered by a rechargeable battery.
Figure 2:
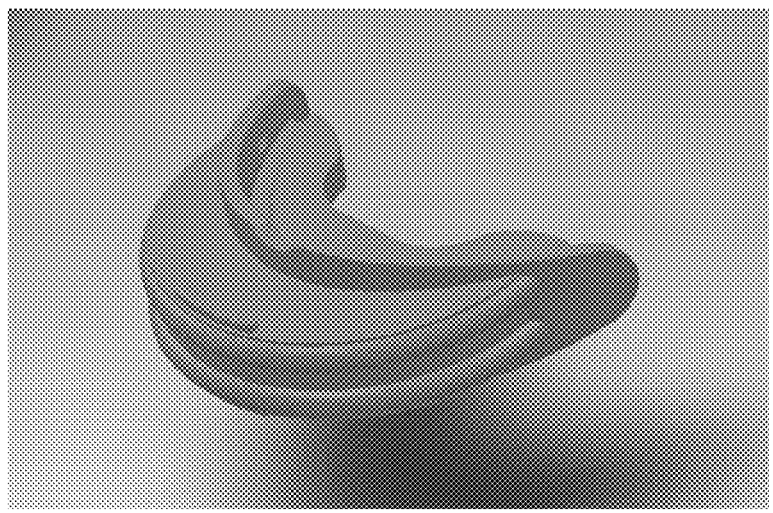
FIG. 2 illustrates the mouthpiece comprising a unique dual cylindrical lens that couples the light from a dual row of LEDs (from the illuminator) precisely onto the teeth. The top and bottom rows of LEDs are focused through the upper and lower cylindrical lens onto the upper and lower row of teeth respectively. The mouthpiece is removable and consumable, and is designed to facilitate light activation of a catalyst without transmitting heat to the teeth.
Figure 3:
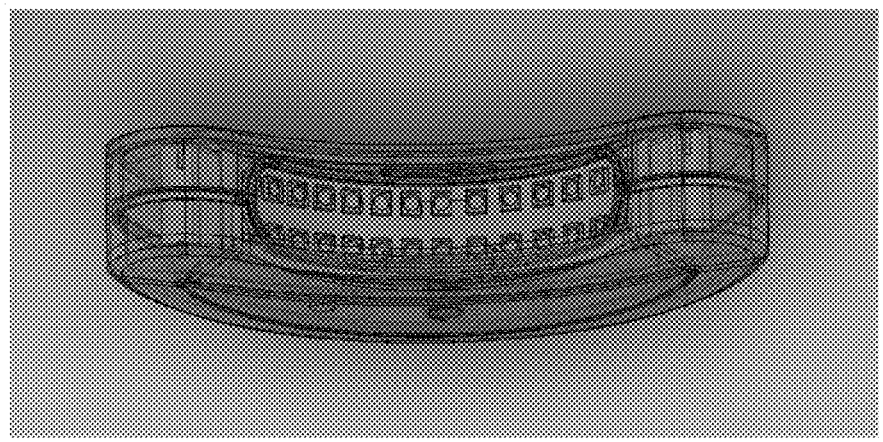
FIG. 3 illustrates the illuminator itself consisting of a novel dual row LED configuration which mates with the dual cylindrical lens array within the mouthpiece. The LEDs are formed into a curved configuration to mate precisely with the curvature of the lens assemblies on the front surface of the mouthpiece.
Figure 4:
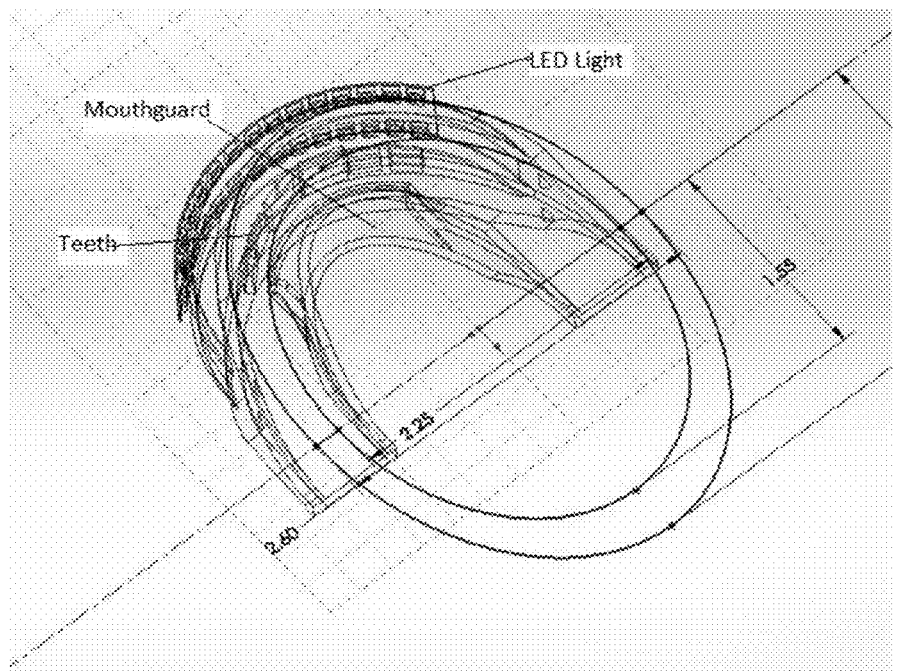
FIG. 4 illustrates the novel optical design of the dual LED array and the dual cylindrical lens mouthpiece which provides optimum irradiance on each row of teeth, and minimizes irradiance on the gums and other soft tissues.
Figure 5:
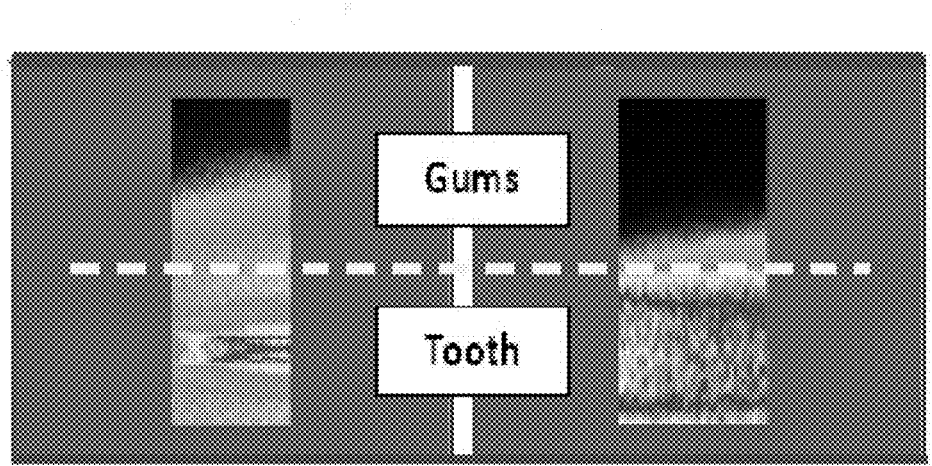
FIG. 5 is an irradiance spectrum demonstrating that the resulting design increases irradiance on the teeth while minimizing irradiance on the gums. The nature of the single axis cylindrical optics is that it also creates high angle irradiance parallel to the direction of the array, which efficiently irradiates the spaces and cracks between the teeth.

The illuminating device of the present disclosure comprises an illuminator LED lightsource that generates a desired intensity, frequency and wavelength of light that is coupled to a removable mouthpiece that acts as the lightguide for precisely directing the light to the teeth.

The light-emitting diode (LED) array is housed in a waterproof or water resistant enclosure which has an optically transmitting faceplate in front of the LED array. The portable lightsource is completely self-contained and includes the LEDs, the rechargeable battery or batteries, all control and recharging electronics, and a heat management system.

The design uses visible light energy for photocatalysis. Ultraviolet light is the most efficacious, but in the preferred embodiment the design uses a blue light at wavelength is 410 nm to about 415 nm, however other more cost-effective and readily available wavelengths may be employed, specifically those in the 400-500 nm range, more preferably within the range 410-470 nm or in the 450-470 nm range. More specifically, the illumination device comprises 28 LED lights (14 per row), which emit a desired light spectrum, preferably emitting blue light at wavelength is 410 nm to about 415 nm.

The present disclosure also relates to the use of the blue light illuminator for the treatment of so-called bad breath or Halitosis. Treatment with blue light with or without whitening conditions for 5 to 10 minutes dramatically improves oral odor. Such treatment may include or be used separately from the whitening procedure. Preferably, a zinc compound (such as zinc chloride, zinc acetate, zinc gluconate or zinc oxide but not limited to) in a range of 0.1% to 25% plus the blue light is even more efficacious for the treatment of oral malodor. It is known that blue light (400 to 500 nm) can help reduce volatile sulfur compounds (anaerobic gram negative bacteria). Zinc is also known to enhance the photo toxicity of blue light against malodor producing bacteria.

Such LED lights typically have substrate based on zinc selenide (ZnSe), indium gallium nitride (InGaN), silicon carbide (SiC) and silicon (Si). The LED lights comprise encapsulated clear or colored molded shells. The shells are designed to boost the light emission from the semiconductor core by acting as a diffusing lens, allowing light to be emitted at a much higher angle of incidence from the light cone than the bare chip is able to emit alone. Light size is designed for maximum tooth illumination. Lights may be of varied size depending on tooth dimensions (molar, incisor, genetically small or large, damaged teeth or gums, etc.). Tooth widths are typically 2-9 mm and thus the LED lights may optionally be of variable size so as to maximally irradiate the tooth surface. The lights are also arrayed along a cylindrical axis in which the emitted light is directed perpendicular to the tooth surface at a distance to maximize the incident intensity. This novel design is further constructed specifically so that the user may perform mobile hands free treatments with no connecting cords or secondary elements.

LED illumination of the catalyst conditioned teeth may lead to so-called recombination of the catalytic dissociation products. To limit such recombination, reagents may be added and/or the light may be turned off to spatially control the localized production of ions. In this novel design the light is made to strobe (turn on and off repeatedly) to reduce the amount of recombination (the combining of substrate charge centers and/or the photocatalytically created reactive species—both of which reduce activity due to recombination). In a preferred embodiment the flashing rate is 33 Hertz with a 5% duty cycle (5% ON time), however the strobe rate can range from 1 Hz to 10 kHz and the duty cycle can range from 1% to 75%. These ranges can be adjusted to maximize the whitening rate by increasing the short term irradiance levels required to drive more instantaneous catalytic events, while at the same time spatially and temporally minimizing recombination events.

The present disclosure also encompasses a novel dual cylindrical lens array coupled with a curved dual LED array. This design combination maximizes the activity at and around the front of the tooth surface, including the cracks and spaces between the teeth. This design also provides superior light distribution to the anterior teeth. It allows for maximum activity at the tooth surface, with minimal activity on the gums and other soft tissue. The lens material may comprise optically clear polyurethane or any optically clear material that transmits blue light including silicone, PMMA (acrylic), polycarbonate, etc.

The present disclosure also encompasses a heat management system that stores the heat within the lightsource so that it is not conducted or radiated to the teeth. Preferably the heat around the teeth is within 1-2 degrees of ambient oral temperature. Normal tooth temperature is about 35 to about 37° C. (95 to 98.6° F.). The thermal reservoir is sufficient in size that it can store the entire heat generated during a treatment regimen.

The present disclosure also allows the user to perform a rapid whitening operation in a completely remote and hands free manner, not requiring a sink or to be connected in any way to any type of cable, tether, control device, power storage pack, or power management device.

The increased whitening rate and efficiency of the present disclosure also refers to the photocatalytic activity of one or more photocatalytic agents added to the oxidizing agent that is applied to the tooth surface before exposure to irradiation. These specific photocatalytic processes and agents have been used in many industries for more than 50 years, and are well known to anyone skilled in the art. In a preferred embodiment the photocatalytic agent is zinc oxide (ZnO) and the oxidizing agent is hydrogen peroxide ($H_2O_2$). The photocatalytic agent may be added to the oxidizing agent before or during the treatment. In a preferred embodiment the ZnO is added to the tooth surface first, and the $H_2O_2$ is applied over the top of the ZnO film. In this manner the catalysis is localized specifically to a thin layer at the surface of the tooth for maximum whitening benefit. This method concentrates the catalytic dissociation of $H_2O_2$ precisely at the tooth surface and further ensures that the bulk of the $H_2O_2$ remains optically transparent so that the light may penetrate to the surface of the tooth for maximum catalytic activity.

The majority of photocatalytic oxidation reactions of this type peak in the ultraviolet (UV) range. Because these UV wavelengths are not desirable for soft tissue exposure, blue wavelengths are employed, but the catalytic conversion efficiency is dramatically decreased at these longer wavelengths. A variety of absorption shifting agents may be used to enhance the efficacy of these longer wavelengths. In a preferred embodiment fluorescein is used because of its existing FDA approval status, but any number or combination of additional absorption shifting elements may be employed.

The catalysis process takes place on the surface of the photocatalytic substrate. In a preferred embodiment this substrate is a small particle of ZnO. In a preferred embodiment these particles are applied in a thin film using a dried atomized powder. However, this film may be applied employed using either hydrophobic, hydrophilic, or amphipathic carriers. The efficiency of a singular conversion is governed by the photon wavelength, and is maximum in the UV range. The rate of conversion is governed by the number of photons and the number of substrate sites. Therefore both the irradiance and ZnO concentrations are increased to significantly higher levels than is normally employed. The present disclosure utilizes an irradiance of between 3.5 to about 20 mW/cm$^2$, more preferably between 5 to about 20 mW/cm$^2$, more preferably 10 to about 15 mW/cm$^2$. One embodiment of the disclosure utilizes an irradiance of about 11-12 mW/cm$^2$. Another embodiment utilizes an irradiance of greater than 5 mW/cm$^2$. ZnO substrate concentrations of between 0.1 to 25% by weight are common. More preferably the substrate concentrations are between 4 to about 10%, more preferably about 4 to about 6%, most preferably about 5%. In another embodiment, the substrate concentration is greater than 10% by weight. In general the specifications for irradiation and substrate concentration may range from 0.1 to 50 mW/cm$^2$ and 0.1 to 100% respectively.

In addition to wavelength and irradiance, there are additional rate limiting factors, the first of which is the size of the substrate particle. A particle size that is similar to the wavelength of light to be absorbed can be more optimal. Another embodiment of the disclosure relates to a method of whitening wherein said zinc oxide is a powder USP in a gel formulation wherein the average zinc oxide particle size is between 0.1 microns to 100 microns, more preferably 0.5 microns to 100 microns, most preferred 10 microns. In another embodiment the particle size is approximately 400-500 nm. This can help increase absorption efficiency, but also helps spatially separate catalytic dissociation to help minimize recombination.

Another embodiment of the disclosure relates to the use of a whitening or bleaching agent such as carbamide peroxide or hydrogen peroxide. The oxidizing agent, preferably hydrogen peroxide, may be formulated as a gel, dentifrice, paste, thin film, strip, liquid, spray, or paint applied to the tooth labial surface and creates an admixture with said zinc oxide at the tooth interface. Another embodiment of the disclosure relates to a method of whitening wherein the concentration of hydrogen peroxide ranges from 0.1 to 38 percent, more preferably 3 to 35 percent by weight. The present disclosure may comprise a variety of different oxidizing agents, peroxide types, and concentrations. The preferred embodiment is 9% $H_2O_2$.

The oxidizing agent may also include the addition of other ionic impurities (singularly or in combination) to boost the generation of active oxidizing agents. These may include sodium chloride, potassium chloride, sodium hydroxide, and a host other such agents known to those skilled in the art, including any mixture thereof.

The present disclosure may also incorporate pre or post treatment of desensitizing agents (singularly or in combination) to minimize the sensitivity commonly experienced. These may include potassium nitrate, potassium citrate, and a host other such agents known to those skilled in the art, including any mixture thereof.

Wax formulations are another specific embodiment of the disclosure. Wax includes synthetic and natural waxes such as paraffins, beeswax, ouricury wax, sugarcane wax, retamo wax, lanolin, petroleum jelly, vegetable waxes (including Bayberry wax, candelilla wax, carnauba wax, Castor wax, Esparto wax, Japan wax, Jojoba oil, Ouricury wax, Rice bran wax or Soy wax). Synthetic fatty acid esters such as cetyl palmitate and myricyl palmitate are additional examples of useful waxes. One specific formulation of water, allyl acrylate copolymer and Hydrogen peroxide is of particular interest.

The present disclosure may also include the use of an activation indicator which can change color upon initiation or completion. This may include methylene blue or other such agents known to those skilled in the art, including any mixture thereof.

The present disclosure may also include post treatment applications including nanoparticle pore sealants, remineralizers, germ fighting compounds, breath fresheners, flavorings and sweeteners, or other such agents known to those skilled in the art, including any mixture thereof.

Another embodiment of the disclosure relates to a method of whitening kit for home use of a whitening agent comprising a composition of zinc oxide, a composition of hydrogen peroxide and a light source.

Another embodiment of the disclosure relates to a method of whitening kit wherein said composition of zinc oxide and said composition of hydrogen peroxide are delivered from a single component with 2 separate chambers that mix upon delivery to the tooth surface. The delivery apparatus for the zinc or peroxide includes syringe, ampoule, or tube. Such apparatus may be opaque so as to prevent damage during storage.

Another embodiment of the disclosure relates to the application of the bleaching formulation wherein the treatment period is from 2-10 minutes, more preferably about 5-7 minutes, more preferably 5 minutes or less. Repeat treatment is also preferred with two to ten sessions being common. More preferably 3-7 sessions (five to seven being most common) are sufficient for achieving desired whiteness. Sessions are typically divided by 24 hrs (six to twelve hours also being very common) but can be longer or shorter depending on individual conditions. Total bleaching time is between 20 to 50 minutes, more preferably 35 minutes total, most preferably 25 minutes (wherein each session is approximately 5 minutes).

The following examples demonstrate methods or uses to successfully whiten a patient's teeth.

Example 1

1. Zinc oxide is painted on teeth labial surface in a gel carrier form with the zinc oxide (USP grade) in a concentration of about 4 to 6% with the size of the particle ranging from about 400 to 500 nm.

2. Hydrogen peroxide gel in a concentration of about 9% is painted on the labial surface of the teeth creating an admixture of the zinc oxide and peroxide at the tooth surface (steps 1 and 2 are interchangeable).

3. An illuminator LED lightsource array coupled with a dual cylindrical lens mouthguard pulsating at a frequency of about 33 Hertz with a 5% duty cycle (5% ON time) and a wavelength of about 415 nm is directed at the tooth surface and away from the oral tissues.

4. After treatment period (e.g., 5, 7, 30 or 35 minutes) the light source is removed. This procedure may be repeated 3-7 consecutive times (such as daily or twice daily) with light source removed after each treatment (e.g., 5, 7, 30 or 35 minutes).

Example 2

The zinc and peroxide components are maintained in two separate chambers of a pen or syringe and mix at the delivery tip as the components are applied to the tooth. Once the zinc and peroxide components have been applied to the teeth a LED light source is directed at the tooth surface and away from the oral tissues.

Example 3

The zinc and peroxide components are maintained in two separate chambers of a pen or syringe or two separate pens or syringes. Zinc oxide (USP grade) is painted on teeth labial surface in a gel carrier form at a concentration of about 4 to 6% with the size of the particle ranging from about 0.5 to 10 microns. Hydrogen peroxide gel in a concentration of about 9% is painted on the labial surface of the teeth on top of the zinc oxide creating an admixture of the zinc oxide and peroxide at the tooth surface. The teeth are then illuminated as described above in Example 1.

There have been shown, described and pointed out, fundamental novel features of the disclosure as applied to the exemplary embodiments thereof, it will be understood that various omissions and substitutions and changes in the form and details of devices and methods illustrated, and in their operation, may be made by those skilled in the art without departing from the spirit or scope of the disclosure. Moreover, it is expressly intended that all combinations of those elements and/or method steps, which perform substantially the same function in substantially the same way to achieve the same results, are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. It is the intention, therefore, to be limited only as indicated by the scope of the claims appended hereto.

What is claimed is:

1. An home use dental illuminating device comprising a self-contained blue light illuminating LED lightsource with a heat management system that stores heat within the light source and that generates light at a wavelength of 410-470 nm with a desired intensity, and frequency of light, the LED lightsource being coupled to a removable mouthpiece that acts as the lightguide for precisely directing the light to the front of the tooth surface and without transmitting heat to the teeth.

2. A device according to claim 1 comprising 28 LED lights.

3. A device according to claim 1 wherein the LED strobes at a flashing rate of from 1 Hz to 10 kHz and the duty cycle can range from 1% to 75%.

4. A device according to claim 1 wherein the LED strobes at a flashing rate of 33 Hertz with a 5% duty cycle.

5. A device according to claim 1 wherein the heat generated around the teeth is within 1-2 degrees of the ambient temperature.

6. A method of tooth whitening comprising:
preconditioning the tooth surface with one or more photocatalytic agents and one or more oxidizing agents, and
irradiating the tooth surface with light from an LED lightsource;
wherein said LED lightsource is a self-contained blue light illuminating device with a heat management system that stores heat within the lightsource and that generates light at a wavelength of 410-470 nm with a desired intensity, and frequency of light, the LED lightsource being coupled to a removable mouthpiece that acts as the lightguide for precisely directing the light to the front of the tooth surface and without transmitting heat to the teeth.

7. A method according to claim 6 wherein said photocatalytic agent is zinc oxide (ZnO).

8. A method according to claim 7 wherein said ZnO concentration is between 0.1 to 25% by weight.

9. A method according to claim 6 wherein said oxidizing agent is hydrogen peroxide ($H_2O_2$).

10. A method according to claim 9 wherein said hydrogen peroxide is 3 to 35 percent by weight.

11. A method according to claim 6 wherein said light from an LED lightsource produces radiant light with an intensity of between 3.5 to about 20 mW/cm$^2$.

* * * * *